United States Patent [19]
Newell

[11] Patent Number: 5,240,008
[45] Date of Patent: Aug. 31, 1993

[54] INFLATION CONTROL APPARATUS FOR AN AUTOMATIC BLOOD PRESSURE GAUGE

[75] Inventor: Scott W. Newell, Ipswich, Mass.

[73] Assignee: Siemens Medical Electronics, Inc., Danvers, Mass.

[21] Appl. No.: 767,761

[22] Filed: Sep. 30, 1991

[51] Int. Cl.⁵ .............................................. A61B 5/02
[52] U.S. Cl. .................................. 128/685; 128/677; 128/682
[58] Field of Search ........................ 138/677–678, 138/679–691, 773, 900; 606/201–204; 417/28, 45, 302

[56] References Cited

U.S. PATENT DOCUMENTS

| | | | |
|---|---|---|---|
| 3,581,734 | 6/1971 | Croslin et al. | 128/2.05 M |
| 3,683,655 | 8/1972 | White et al. | 128/30.2 |
| 4,024,864 | 5/1977 | Davies et al. | 417/45 |
| 4,167,181 | 9/1979 | Lee | 128/682 |
| 4,178,918 | 12/1979 | Cornwell | 128/682 |
| 4,360,029 | 11/1982 | Ramsey, III | 128/681 |
| 4,378,807 | 4/1983 | Peterson et al. | 128/677 |
| 4,469,099 | 9/1984 | McEwen | 606/202 |
| 4,493,326 | 1/1985 | Hill et al. | 128/680 |
| 4,625,277 | 11/1986 | Pearce et al. | 364/416 |
| 4,660,567 | 4/1987 | Kaneko et al. | 128/682 |
| 4,715,849 | 12/1987 | Gion et al. | 606/203 |
| 4,735,213 | 4/1988 | Shirasaki | 128/681 |
| 4,949,710 | 8/1990 | Dorsett et al. | 128/680 |
| 5,022,403 | 6/1991 | LaViola | 128/680 |
| 5,144,956 | 9/1992 | Souma | 128/682 |

*Primary Examiner*—Randall L. Green
*Assistant Examiner*—P. Zuttarelli
*Attorney, Agent, or Firm*—Lawrence C. Edelman

[57] ABSTRACT

An automatic blood pressure measuring device includes a flexible inflation system which quickly and accurately inflates neonatal, pediatric and adult cuffs without significant pressure overshoot. The device uses an electric pump having two intake orifices. A restricted orifice provides air to the pump for all cuff sizes. An unrestricted orifice, which may be opened or closed by actuating a valve, provides air to the pump only when an adult or pediatric cuff is being used. In addition, the pump is controlled by a motor controller which provides dynamic breaking to stop the pump quickly when the threshold pressure has been reached. An overpressure mechanism, separate from the pressure sensor that controls the pump, removes operational power from the pump when a predetermined cuff pressure level, greater than the threshold pressure, has been reached.

9 Claims, 2 Drawing Sheets

INFLATION CONTROL APPARATUS FOR AN AUTOMATIC BLOOD PRESSURE GAUGE

BACKGROUND OF THE INVENTION

The present invention is directed to apparatus and a method for automatically measuring the blood pressure of an individual and specifically to apparatus and a method for inflating a pressurized cuff to reliably achieve a predetermined initial pressure level.

A conventional automatic blood pressure gauge includes a resilient inflatable cuff and an electric pump. The pump is controlled by a microprocessor to inflate the cuff with a fluid, such as air, to a preset pressure. In addition, this automatic gauge includes a pressure transducer that measures the instantaneous air pressure levels in the cuff. The pressure signal produced by the transducer is used to determine both the instantaneous air pressure of the cuff and the blood pressure pulse of the individual. This pressure signal is generally digitized and processed by the microprocessor to produce values representing the systolic and diastolic blood pressure measurements of the individual.

In operation, the cuff is affixed to the upper arm area of the patient and is then inflated to a pressure greater than the suspected systolic pressure, for example, 150 to 200 millimeters of mercury (mmHg). This pressure level collapses the main artery in the arm, effectively stopping any blood flow to the lower arm. Next, the cuff is deflated slowly and the transducer pressure signal is monitored to detect variations in cuff pressure caused by the patient's pulse, which is coupled into the cuff. By monitoring the amplitude of the measured pulse signal, the system can determine the patient's systolic and diastolic pressures.

One exemplary system is described in U.S. Pat. No. 4,949,710 entitled METHOD OF ARTIFACT REJECTION FOR NONINVASIVE BLOOD-PRESSURE MEASUREMENT BY PREDICTION AND ADJUSTMENT OF BLOOD-PRESSURE DATA, which is hereby incorporated by reference for its teaching on automatic blood pressure gauges. This system monitors the patient's blood pressure signal to determine the maximum detected pulse amplitude. This is commonly referred to as the mean arterial pressure (MAP). The systolic and diastolic blood pressure levels are then determined as the respective pressures corresponding to the amplitude of the pulse signal being 60% of the maximum value, prior to reaching the maximum value; and 80% of the maximum value, after reaching the maximum value.

To be most effective, an automatic blood pressure gauge should quickly inflate the cuff to a preset pressure value and then deflate the cuff according to a known deflation curve. It is desirable to complete this task in a relatively short time period, so as to provide quick results and to minimize patient anxiety and discomfort. This task is complicated by differences in blood pressure from person to person and in one person within a single day. For example, the systolic blood pressure of an individual may range between 90 mmHg and 180 mmHg in a single day between periods of sleep and periods of exercise.

Another factor to be considered is the adaptability of the blood pressure gauge. To be as useful as possible, it is desirable for the gauge to operate well with a number of different types of cuffs. These include neonatal cuffs for infants and finger, arm and thigh cuffs for children and adults. Each of these types of cuff may hold a different amount of fluid when inflated to a given pressure. To be generally useful, it is desirable for the blood pressure gauge to inflate each type of cuff to the preset pressure within a predetermined time interval with approximately the same level of accuracy. It is also important that the gauge not overinflate any of the cuffs, especially the small pediatric and neonatal cuffs.

It is desirable to inflate an adult cuff to its initial pressure in five to six seconds. The fluid flow which produces this inflation rate in a large cuff may be too great for very small cuffs, such as those used for neonates. If this flow rate were used for all cuffs, the combined effects of the delay in measuring and in responding to the threshold pressure level, and the inertia in the pump and pump motor may combine to cause pressures much greater than the threshold pressure to be applied to a neonatal cuff.

U.S. Pat. No. 4,493,326 entitled AUTOMATIC BLOOD ? 0 PRESSURE SYSTEM WITH SERVO CONTROLLED INFLATION AND DEFLATION, which is hereby incorporated by reference, operates the pump motor under closed-loop servo control. Signals generated by a pressure gauge coupled to the cuff are used to control the pump motor to maintain a constant inflation rate. The pump is turned off when the level of the pressure signal exceeds a predetermined threshold. The time required to inflate a cuff with this system depends on the volume of the cuff and the selected inflation rate. If the rate is too fast, it is possible that a small cuff, for example, a neonatal cuff, may be over inflated before the system can stop the pump. If the rate is too slow, it may take a relatively long time to inflate a large cuff, such as a thigh cuff, to the desired threshold pressure.

U.S Pat. No. 4,360,029 entitled AUTOMATIC MEAN BLOOD PRESSURE READING DEVICE, which is hereby incorporated by reference, inflates the cuff to a pressure which is 60 mmHg greater than the previously measured mean arterial pressure (MAP). The MAP is the pressure at which the blood pressure pulse signal sensed by the blood pressure gauge has its greatest value. If no value for MAP has previously been determined, the gauge stops the pump when a pressure of 160 mmHg has been reached.

SUMMARY OF THE INVENTION

The present invention is embodied in an automatic blood pressure measurement device which may be used to quickly and accurately inflate a variety of different cuffs to a desired pressure level. The device includes a small orifice having a relatively slow flow rate and a large orifice having a higher flow rate but which may be opened or closed by a controlled valve. Fluid may be supplied to the pump through one or both of these orifices depending on the setting of the valve. For cuffs having a small volume, the valve is closed and the fluid supplied to the pump comes only through the small orifice. This ensures that the cuff is inflated at a relatively low rate. For cuffs having a larger volume, the valve is opened and fluid is supplied to the pump through the large orifice, allowing the cuff to be inflated at a relatively high rate.

According to another aspect of the invention, the automatic blood pressure device uses an electric pump having a relatively low inertia and employs control circuitry which applies dynamic breaking to the pump motor when the predetermined initial pressure level has been reached.

According to yet another aspect of the invention, the device includes an overpressure sensor which, when an overpressure condition is detected, removes power from the pump motor.

DETAILED DESCRIPTION OF THE INVENTION

Figure 1:
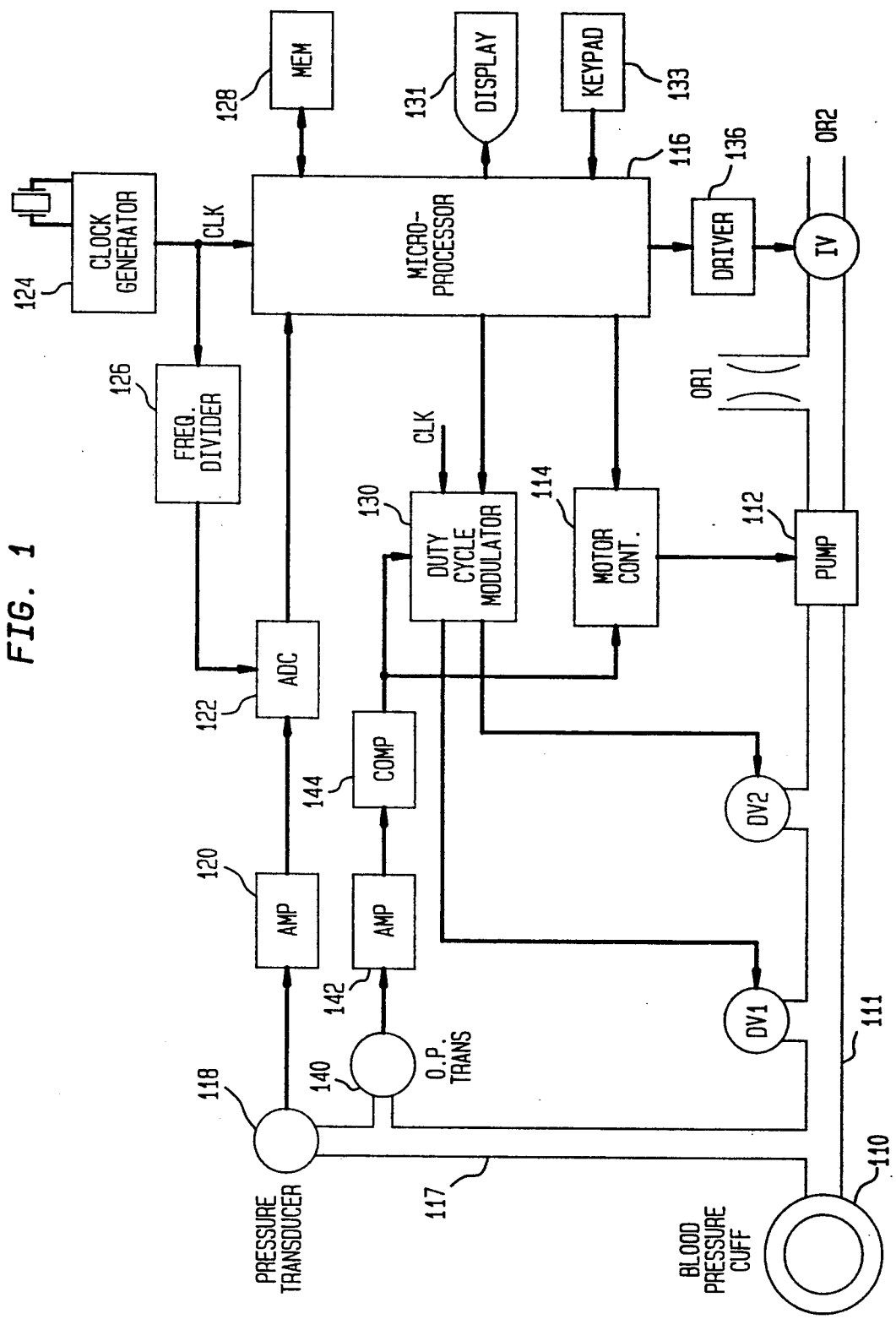
FIG. 1 is a block diagram of an automatic blood pressure measurement system in accordance with the present invention.

FIG. 1 is a block diagram of an exemplary automatic blood pressure gauge according to the present invention. This gauge includes a conventional blood pressure cuff 110 which may be inflated by an electric pump 112 using an air channel 111. The pump motor is turned on and off by a motor controller 114 which is responsive to signals provided by a microprocessor 116. A suitable pump for use in this embodiment of the invention is a diaphragm type, driven by a low inertia DC motor. The motor controller is described in detail below with reference to FIG. 2.

Air is supplied to the pump 112 through an orifice, OR1 which has a restricted flow and through an orifice, OR2 which, although unrestricted, may be selectively blocked by closing a solenoid activated inflation valve IV in series with the orifice OR2 and the intake port of the pump 112. The inflation valve IV is controlled by the microprocessor 116 via driver circuitry 136 as described in detail below.

The cuff is deflated using two digitally controlled solenoid valves, DV1 and DV2. When open, the valve DV1 has a relatively low flow rate, and the valve DV2 has a relatively high flow rate. In this embodiment of the invention, the valves are controlled by a pulse width modulated signal having a set nominal frequency.

A microprocessor 116 controls the valves DV1 and DV2 using a duty cycle modulator 130. The modulator 130 produces a variable duty cycle oscillatory signal which controls a selected one of the valves DV1 and DV2. The duty cycle of this signal is controlled to determine the effective aperture of the selected valve, and thus, the rate at which the cuff 110 is deflated.

The microprocessor 116 monitors the air pressure in the cuff using a conventional pressure transducer 118 which is coupled to the air channel 111 via a tube 117. In the exemplary embodiment of the invention, the pressure transducer is of the conventional semiconductor strain gauge type. The signal produced by the transducer 118 is amplified by a low-noise instrument quality amplifier 120 which produces a signal that is applied to an analog to digital converter (ADC) 122. In this embodiment of the invention, the ADC 122 is a 16-bit sigma-delta type analog to digital converter. The ADC 122 produces samples at a rate of approximately 50 Hz. A frequency divider 126 is coupled to receive an 8 MHz clock signal CLK provided by a resonant crystal controlled clock signal generator 124. This signal is divided in frequency as needed to produce the clock signal for ADC 122.

The sampled data pressure signal provided by the ADC 122 is monitored by the microprocessor 116 to start the pump when a pressure measurement has been made; to stop the pump 112 when the desired initial cuff pressure has been obtained; to control the flow through the deflation valves DV1 and DV2; and to extract, from the pulse signal, the systolic and diastolic blood pressure measurements for the individual.

The automatic blood pressure gauge shown in FIG. 1 includes a second pressure transducer, 140, which may be identical to the pressure transducer 118. The transducer 140, however, is only used by the system to detect overpressure conditions. As shown in FIG. 1, the output signal provided by the transducer 140 is amplified by an amplifier 142 which may be identical to the amplifier 120, described above. The amplified output signal is applied to a comparator 144. The comparator 144 provides a logic-high output signal only when the signal from the amplifier 142 indicates that the cuff pressure is greater than a preset overpressure threshold. In the exemplary embodiment of the invention, this threshold is set to 300 mmHg.

The output signal of the comparator 144 is applied to the duty cycle modulator 130 and to the motor controller 114. When an overpressure condition is detected, the motor controller 114 stops the pump motor, and the duty cycle modulator opens both of the deflation valves DV1 and DV2. These control functions are performed without using the microprocessor 116 in order to provide effective control in instances where a fault in the microprocessor has caused the overpressure condition.

The blood pressure measurements are presented to the operator on a display device 131. To produce these values, the microprocessor 116 operates under the control of a program stored in the memory 128. The memory 128 also contains cells which may be used for storing temporary data values. In the exemplary embodiment of the invention, the program storage portion of the memory 128 is a read-only memory (ROM) while the data storage portion is a random-access memory (RAM).

Operator commands to the blood pressure gauge are provided to the microprocessor 116 via a keypad 133. The two commands of greatest importance to this embodiment of the invention are the command which defines the type of cuff being used (neonatal or adult) and the command to begin a blood pressure measurement.

The microprocessor 116 captures samples produced by the ADC 122 at a 50 Hz rate. The collected samples are processed in groups of 45 to obtain a noise-reduced cuff pressure signal and its first derivative, representing the actual rate of change of the cuff pressure. These signals have an effective sampling rate of 1.11 Hz. While the cuff 110 is being inflated, the microprocessor 116 determines if the pump 112 should be stopped for each sample of this signal. While the cuff is being deflated, the microprocessor 116 uses this signal to calculate new settings for the deflation valve DV1 or DV2. The microprocessor 116 controls the deflation valves DV1 and DV2, through the duty cycle modulator 130 to release fluid from the cuff at a constant rate in order to achieve a linear reduction in cuff pressure.

Figure 2:
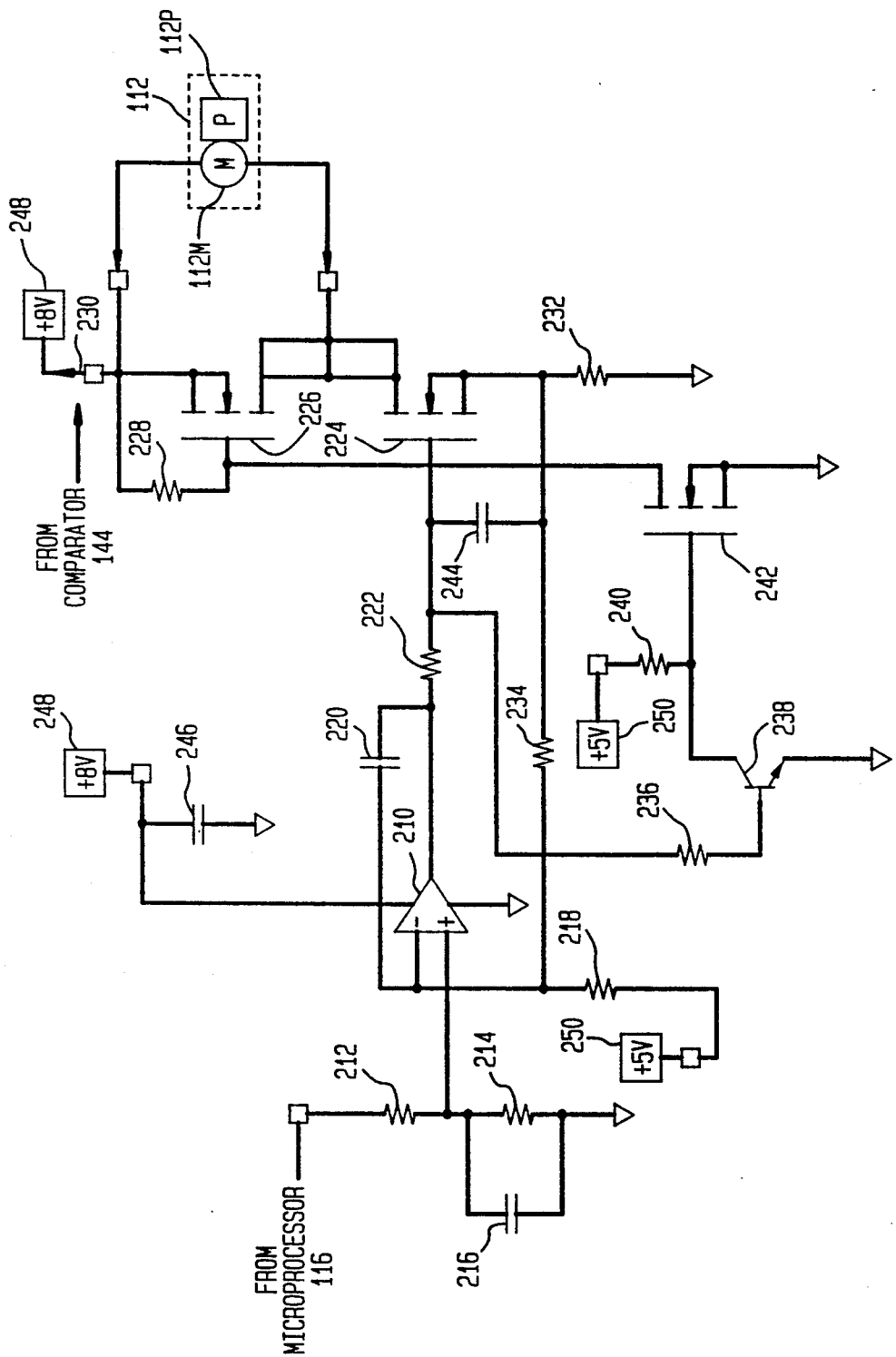
FIG. 2 is a schematic diagram, partly in logic diagram form of a motor controller suitable for use in the automatic blood pressure measurement system shown in FIG. 1.

FIG. 2 is a schematic diagram of exemplary circuitry suitable for use as the motor controller 114. This circuitry includes a closed-loop feedback controller which limits the current drawn by the pump motor 112m to be less than 300 milliamperes (ma). In addition, the controller includes circuitry which applies dynamic breaking to the motor 112m in response to a stop signal from the microprocessor 116. By limiting the maximum current that can be drawn by the motor, the motor controller 114 allows a lower power and thus, less expensive power supply to be used in the blood pressure gauge. By rapidly stopping the pump motor, the controller 114 allows the gauge to more accurately control the inflation pressure. This is especially important for neonatal cuffs and small pediatric cuffs.

The control signal from the microprocessor 116 is a two-valued signal: logic-high when the pump is to run and logic-low when the pump is to stop. This signal is applied to one end of a voltage divider circuit which includes the resistors 212 and 214. The resistor 214 is coupled to a source of reference potential (e.g. ground) in parallel with a capacitor 216. The combination of the resistor 214 and the capacitor 216 form a low-pass filter which removes high frequency components from the control signal so that the control circuitry does not attempt to turn on the motor too quickly.

The junction of the resistors 212 and 214 is connected to the noninverting input terminal of an operational amplifier 210. The operational amplifier 210 is configured as an integrator with a capacitor 220 coupled between its inverting input terminal and its output terminal. The inverting input terminal of the amplifier 210 is coupled to receive an input signal from a biasing network which includes the resistors 218 and 234. Resistor 218 is coupled to a source of operational potential 250, which, in the exemplary embodiment of the invention is a five volt source. A sense resistor 232, coupled between the resistor 234 and ground, applies an input signal to the inverting input of the amplifier 220 by changing the potential at the junction of the resistors 218 and 234 based on the current drawn by the motor 112m.

Operational power is applied to the amplifier 210 by connections to a source of eight-volt operational potential 248 and to ground. A capacitor 246 is coupled between the source 248 and ground to filter out transient signals imposed on the eight-volt operational power signal that may be caused, for example, by the motor 112m and to provide a low impedance supply at high frequencies to the operational amplifier 210.

The output terminal of the operational amplifier 210 is coupled to the gate electrode of a transistor 224 through a resistor 222. Capacitor 244 absorbs the drain-to-gate coupled charge of transistor 224 when transistor 226 is turned on. This prevents parasitic turn-on of transistor 224 at that moment. The drain electrode of the transistor 224 is coupled to one terminal of the motor 112m while the source electrode of the transistor is coupled to ground through the resistor 232. The other terminal of the motor 112m is coupled, through a switch 230, to the operational power source 248. The switch 230 is controlled by the overpressure output signal provided by the comparator 144, shown in FIG. 1. When the output signal of the comparator 144 becomes logic-high, indicating that an overpressure condition has been detected, the switch 230 is opened, removing operational power from the pump motor 112m.

In addition to the basic control circuitry, described above, the motor controller also includes circuitry which implements a dynamic breaking function for the motor 112m. This circuitry includes a bipolar transistor 238, field effect transistors 226 and 242, and resistors 228, 236 and 240. The transistor 226 provides a low resistance between the terminals of the motor 112m when the motor is to be stopped. In this configuration, the motor 112m acts as a generator driving a low impedance load, producing a dynamic breaking effect.

In steady state, when the signal provided by the microprocessor 116 is logic-low, the non-inverting input terminal of the operational amplifier 210 is at ground potential, and a direct current (DC) potential of approximately 50 millivolts (mv) is applied to the inverting input terminal. In this configuration, the amplifier 210 provides an output signal at ground potential. This signal turns the transistor 224 off, breaking the connection between the motor 112m and ground. In addition, the output signal of the amplifier 210 turns the bipolar transistor 238 off, causing the transistors 242 and 226 to be turned on. When transistor 226 is turned on, it effectively shorts out the motor 112m.

When the control signal from the microprocessor 116 undergoes a transition from logic-low to logic-high, the signal applied to the non-inverting input of the amplifier 210 undergoes a more gradual transition from ground potential to approximately 150 mv. The speed of this transition is determined by the low-pass filter 214, 216. As the level of this signal rises above 50 mv, the output signal provided by the amplifier also rises. The first effect of this rising output signal is to turn on the transistor 238. This causes the transistors 242 and 226 to turn off. As the output signal of the amplifier 210 rises to a higher level, transistor 224 turns on, allowing current to flow through the motor 112m.

As the potential applied to the gate electrode of the transistor 224 rises, the motor 112m starts to turn. As is well know, a DC motor draws relatively more current when it is starting up than when it is running at a steady speed. In the circuit shown in FIG. 2, the extra current drawn by the motor when it is running at low speed causes the potential across the resistor 232 to rise, increasing the potential applied to the inverting input of the amplifier 210. The increased potential on the inverting input terminal tends to reduce the level of the signal applied to the gate electrode of the transistor 224, limiting the level of current that may be drawn by the motor. In this configuration, the current drawn by the motor is limited to approximately 300 ma. As the speed of the pump motor increases, the current that it draws falls well below 300 ma.

When the signal provided by the microprocessor 116 falls to a logic-low value, the potential applied to the non-inverting input of the amplifier 210 falls at a rate determined by the low pass filter 214, 216. As this potential falls below 50 mv, the output signal provided by the amplifier 210 approaches ground potential. The potential stored on the capacitor 244 is dissipated relatively quickly through the resistor 222. Consequently, the potential applied to the gate electrode of transistor 224 is relatively quickly reduced, causing the transistor to cut off current to the pump motor 112m.

After the transistor 224 has been turned off, the potential across the capacitor 244 decreases further until the base-emitter junction of the transistor 238 is no longer forward biased, turning off the transistor 238. As the transistor 238 is turning off, the potential at the gate electrode of transistor 242 rises, turning on transistor 242. When transistor 242 is turned on, the potential at the gate electrode of transistor 226 approaches ground potential, producing a low impedance path between the source and drain electrodes of the transistor and, thus, between the power terminals of the motor 112m.

This low impedance path causes the DC motor 112m to act as a generator, producing a dynamic breaking effect in the motor. Thus the motor stops more quickly than if power is simply removed from the power terminals.

Referring to FIG. 1, when the operator indicates, via the keypad 133, that the cuff 110 is a neonatal cuff, the microprocessor 116 applies a signal to the driver 136 causing it to close the inflation valve IV. In this configuration, restricted orifice OR1 is the only source of air for the pump 112. Using only the restricted orifice OR1, neonatal cuffs inflate in 1 to 8 seconds.

When the operator indicates that the cuff 110 is a pediatric or adult cuff, the microprocessor 116 conditions the driver 136 to open the valve IV. This increases the pump flow approximately by a factor of five. With both valves open the smallest pediatric cuffs inflate in about 1 second and the largest adult cuffs inflate in about 10 seconds.

In the exemplary embodiment of the invention operator indicates, using the keypad 133, that the cuff is a neonatal cuff or a pediatric or adult cuff. Based on this indication, the microprocessor 116 either opens or closes the inflation valve IV. Alternatively, the microprocessor may automatically determine the type of cuff. As set forth above, part of the control process is to determine the volume of the cuff when it is being inflated to its initial pressure. It is contemplated that this initial volume determination may be used during the inflation process to dynamically determine whether valve IV should be opened or closed.

As set forth above, the overshoot in pressurizing the cuff is an important factor. When the motor controller is used which does not have dynamic breaking but which is otherwise equivalent to the controller shown in FIG. 2, the inventors measured pressure overshoots as high as 22 mmHg for neonatal and small pediatric cuffs. With the dynamic breaking circuitry, the maximum overshoot for these cuffs is reduced to approximately 8 mmHg.

Table 1 lists exemplary values for the components in the motor controller circuit shown in FIG. 2.

TABLE 1

| Component | Value |
|---|---|
| 112 m | escap TM 22C11 |
| 210 | LM358 |
| 212 | 332 kΩ |
| 214, 228, 234, | 10 kΩ |
| 216 | 0.068 μF |
| 218 | 1M Ω |
| 220 | 330 pF |
| 222 | 1 kΩ |
| 224 | BSP295 |
| 226 | BSP315 |
| 232 | 0.33 Ω |
| 236, 240 | 24.9 kΩ |
| 238 | 2N3904D |
| 242 | BSS119 |
| 244 | 0.01 μF |
| 246 | 0.1 μF |

The exemplary inflation control system described above includes an electric pump which draws air from a restricted orifice, an unrestricted orifice that may be either opened or closed by a controlled valve. In addition, the system includes motor controller circuitry which implements dynamic breaking for the motor to minimize pressure overshoot when the pump is stopped. The inflation control system can also sense when the pressure has exceeded an overpressure threshold. In this instance, circuitry directly connected between the overpressure sensor, the motor controller and a controller for the deflation valves, stops the motor and opens both deflation valves when an overpressure condition is detected.

While this invention has been described in terms of an exemplary embodiment, it is contemplated that it may be practiced as outlined above within the scope of the appended claims.

The invention claimed is:

1. An inflation system for automatically pressurizing one of at least two blood pressure cuffs of respectively different sizes with a fluid, comprising:
    at least two blood pressure cuffs of respectively different sizes;
    an electric pump means having an input port for receiving said fluid and through which said fluid is provided to said electric pump means and an output port through which said fluid is provided from said electric pump means to a selected one of said at least two blood pressure cuffs which is coupled to said output port of said electric pump means;
    first orifice means, including a first fluid communication path coupled to said electric pump means for limiting the fluid flow provided by said electric pump means to said selected blood pressure cuff so that it does not exceed a first rate;
    second orifice means, including a second fluid communication path coupled to said electric pump means for limiting fluid flow provided by said electric pump means to said selected blood pressure cuff so that it does not exceed a second rate, greater than the first rate;
    means for determining a desired inflation rate for the selected blood pressure cuff and providing a control signal in response to said determination; and
    valve means located in said second fluid communication path and responsive to said control signal for selectively blocking said second fluid communication path so as to cause inflation of the selected blood pressure cuff with said fluid at substantially the first rate or the second rate depending on which one of said at least two blood pressure cuffs of respectively different sizes is coupled to said electric pump means.

2. An inflation system according to claim 1 wherein:
    the electric pump means includes first and second terminals thereon for applying an operational power signal to the electric pump means; and
    the inflation system further comprising:
    pressure measuring means coupled to and in fluid communications with said selected blood pressure cuff for emitting an output signal when the selected blood pressure cuff is pressurized to a predetermined pressure level; and
    motor controller means, coupled to the electric pump means and responsive to the output signal of the pressure measuring means, for coupling a low resistance path between the first and second terminals of the electric pump means in response to the output signal, to produce a dynamic braking effect in the electric pump means caused by a back electromotive force generated thereby, said dynamic breaking effect assisting the electric pump means to rapidly cease its pumping operation.

3. An inflation system according to claim 2 wherein the motor controller means further includes means for controlling the operational power signal applied to the electric pump means to ensure that a current component of the operational power signal does not exceed a predetermined threshold value.

4. An inflation system according to claim 2 further comprising:

further pressure measuring means coupled to and in fluid communication with said selected blood pressure cuff means for emitting an overpressure output signal when the selected blood pressure cuff is pressurized to an overpressure level greater than a predetermined maximum pressure level; and means coupled to the motor controller means and responsive to the overpressure output signal for disconnecting operational power from at least one of the first and second terminals.

5. A system for automatically inflating a blood pressure cuff with a fluid to a predetermined pressure level, comprising:

a blood pressure cuff;

electric pump means, having first and second terminals which selectively receive an operational power signal, and a fluid flow path coupled between a fluid reservoir, said pump, and the blood pressure cuff for providing fluid to inflate the blood pressure cuff coupled thereto when said operational power signal is received by the first and second terminals of the electric pump means;

pressure sensor means, coupled to and in fluid connection with the blood pressure cuff, for providing a pressure signal indicating when fluid in the blood pressure cuff has reached said predetermined pressure level; and motor controller means, coupled to the first and second terminals of the electric pump means and responsive to the pressure signal, for coupling a low resistance path between the first and second terminals of the electric pump means when the pressure signal indicates that said predetermined pressure level has been reached, to produce a dynamic braking effect in the pump caused by a back electromotive force generated thereby, said dynamic breaking effect assisting the electric pump to rapidly cease its pumping operation.

6. A system according to claim 5 wherein the fluid flow path of the electric pump means includes an intake port coupled to and in fluid connection with the reservoir of said fluid and an output port coupled to and in fluid connection with the blood pressure cuff, the system further including:

a first fluid flow orifice, coupled to said electric pump means, limiting the fluid flow to the blood pressure cuff at a first rate;

a second fluid flow orifice, coupled to said electric pump means, for limiting the fluid flow to the blood pressure cuff at a second rate, greater than the first rate;

valve means, coupled to the second fluid flow orifice and responsive to a control signal, for selectively blocking fluid flow through the second fluid flow orifice; and control means, responsive to operator commands, for generating the control signal and thereby determine the flow rate at which fluid is supplied to the blood pressure cuff.

7. A system according to claim 5 wherein the motor controller means further includes means for controlling the operational power signal applied to the electric pump means to ensure that a current component of the operational power signal does not exceed a predetermined threshold value.

8. A system according to claim 5 further comprising:

further pressure sensor means coupled to the blood pressure cuff for emitting an overpressure output signal when the cuff is pressurized to an overpressure level greater than a predetermined maximum pressure level; and means coupled to the motor controller means and responsive to the overpressure output signal for disconnecting the operational power signal from at least one of the first and second terminals of the electric pump means.

9. An automatic blood pressure gauge, comprising:

a neonatal cuff having a relatively small size and an adult cuff having a relatively large size;

inflation means coupled between a reservoir of fluid and a selected one of said neonatal cuff or said adult cuff for inflating said selected cuff with said fluid;

inflation control means coupled to said inflation means for controlling inflation of said selected cuff by said inflation means;

cuff size sensing means included in said inflation means for producing an output signal indicating that the inflation means is connected to a neonatal cuff or to an adult cuff;

a first fluid flow orifice, connected to and in fluid connection with said inflation means and said selected cuff, through which the inflation means provides fluid to the selected cuff at a first rate;

a second fluid flow orifice, connected to and in fluid connection with said inflation means and said selected cuff, through which the inflation means provides fluid to the selected cuff at a second rate, greater than the first rate; and valve means, coupled to the second fluid flow orifice and responsive to the output signal provided by the cuff size sensing means for selectively opening or closing the second orifice so that fluid can or can not be provided therethrough, respectively, when the selected cuff is an adult cuff or a neonatal cuff, respectively.

* * * * *